United States Patent [19]

Kotz et al.

[11] Patent Number: 4,563,344

[45] Date of Patent: Jan. 7, 1986

[54] CONTROLLED RELEASE AGGLOMERATED CARRIER

[75] Inventors: Michael E. Kotz, Toledo; Jacobus J. Van der Zwan, Perrysburg, both of Ohio

[73] Assignee: The Andersons, Maumee, Ohio

[21] Appl. No.: 481,905

[22] Filed: Apr. 4, 1983

[51] Int. Cl.$^4$ .................... A01N 25/00; A01N 63/00; A01M 1/20

[52] U.S. Cl. ........................................ 424/17; 424/93; 514/89; 514/951; 43/132.1

[58] Field of Search ............. 424/362, 93, 16, 17, 424/19, 200; 71/23, 3; 43/132.1; 422/37; 239/53, 54

[56] References Cited

U.S. PATENT DOCUMENTS

| | | | |
|---|---|---|---|
| 879,877 | 2/1908 | Kennedy | 71/23 |
| 2,974,030 | 3/1961 | Geary | 71/3 |
| 3,034,882 | 5/1962 | Renwick | 71/23 |
| 3,161,497 | 12/1964 | Amburn | 71/112 |
| 3,172,752 | 3/1965 | Pierce | 71/62 |
| 3,252,785 | 5/1966 | Hoblit | 71/23 |
| 3,502,458 | 3/1970 | Schenk | 71/64 |
| 3,953,191 | 4/1976 | Barton | 71/23 |
| 4,053,112 | 10/1977 | Vander Hooven et al. | 241/24 |
| 4,166,112 | 8/1979 | Goldberg | 424/93 |
| 4,247,403 | 1/1981 | Foley et al. | 252/8.5 LC |

OTHER PUBLICATIONS

*Corncob Fractions in Animal Rations,* Published by The Andersons of Maumee, Ohio.
*Bed-o'cob® Laboratory Animal Bedding,* Published by The Andersons of Maumee, Ohio.
Merck Index, 9th Ed., #2179.
Coppedge et al., J. Econ. Entomol., 67(2), 1974, 292–294.
Mulla, Down to Earth, vol. 23, No. 2, pp. 15–17, Fall 1967.
Banks et al., J. Econ. Entomol., 66(1), 1973, 241–244.

*Primary Examiner*—Sidney Marantz
*Assistant Examiner*—Shawn P. Foley
*Attorney, Agent, or Firm*—Emch, Schaffer, Schaub & Procello Co.

[57] ABSTRACT

A controlled release agglomerated carrier for pesticides and the like comprised of preselected portions of the pith, fine and coarse chaff and woody ring portions of a corncob which, when combined in varying ratios, define an overall release rate for the carrier and/or act as a bait for the targeted species.

25 Claims, 3 Drawing Figures

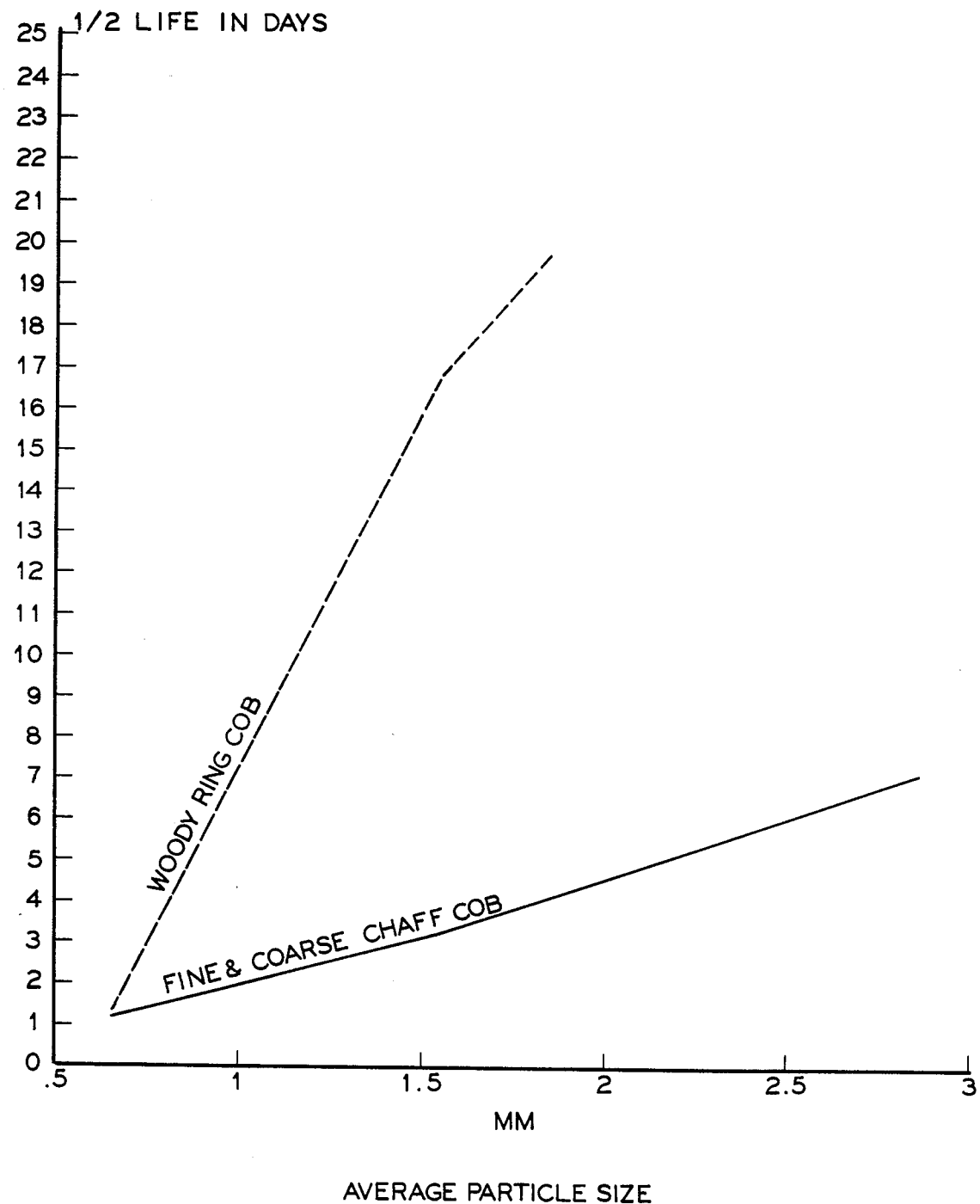

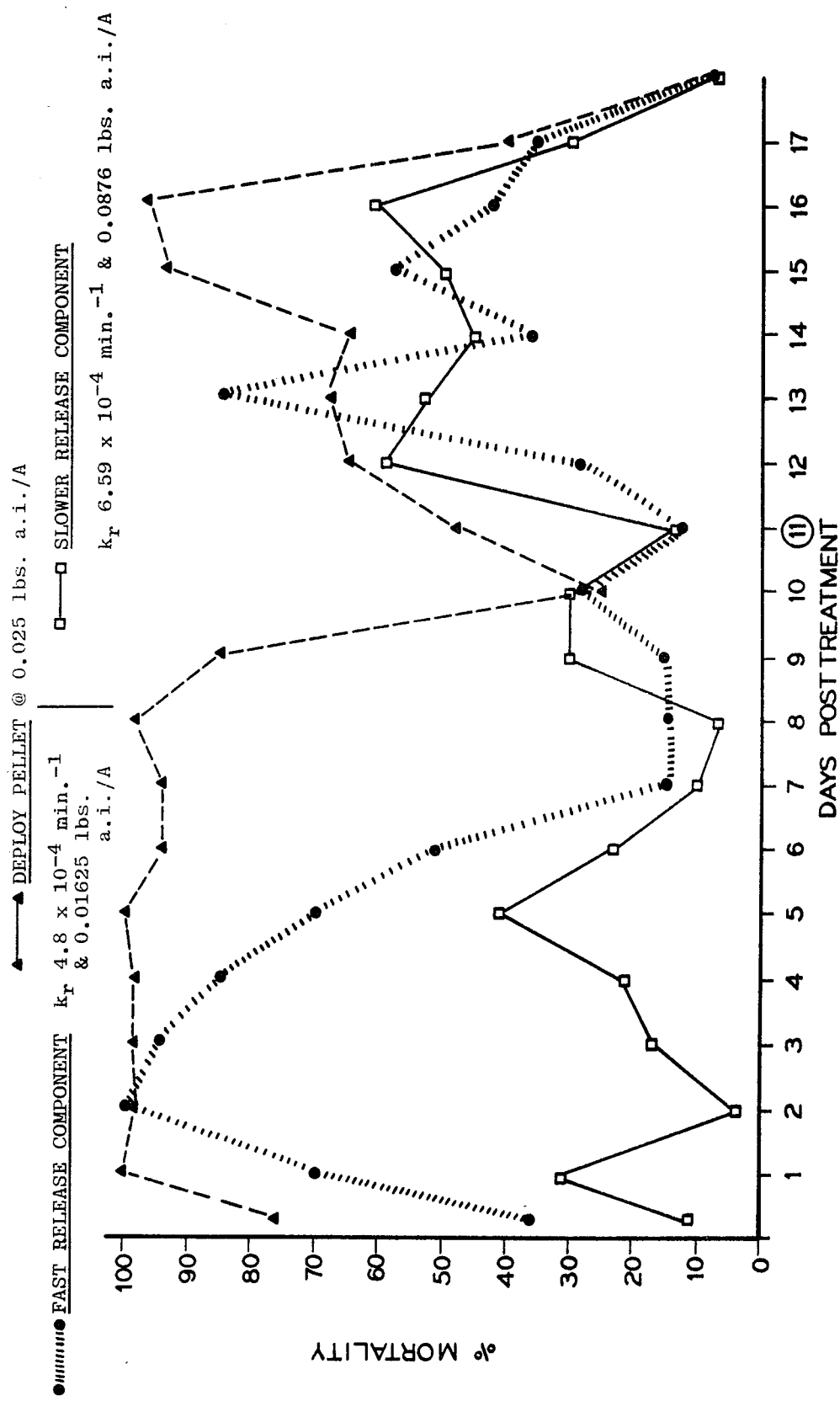

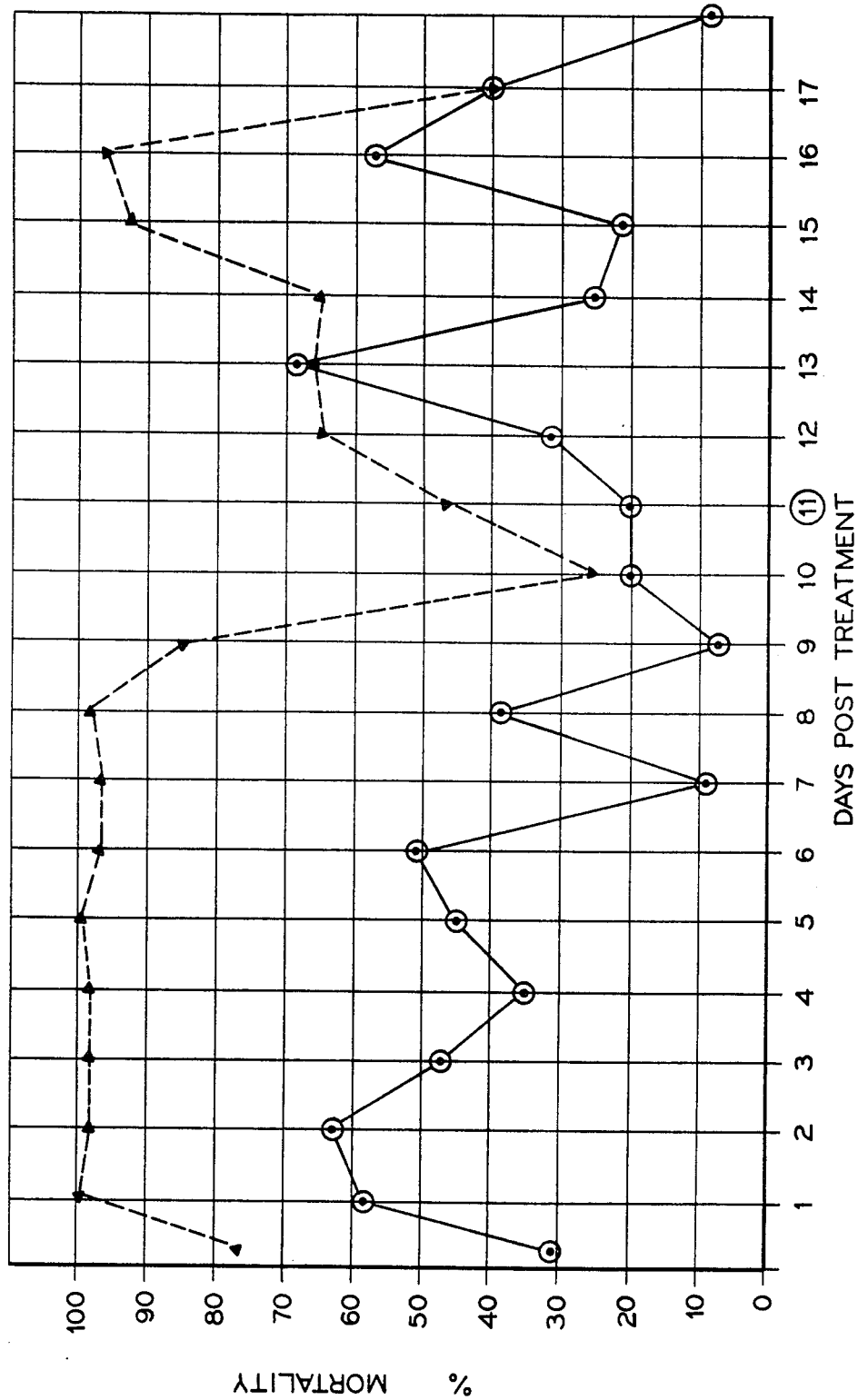

CONTROLLED RELEASE AGGLOMERATED CARRIER

BACKGROUND OF THE INVENTION

The effectiveness of solid form pesticides is dependent not only upon the active ingredient but also upon the inert ingredient used as the carrier for the active. The inert carrier acts as the transfer mechanism for the active ingredient. If the carrier does not effectively release the active, the active will never reach its intended target. Thus, the development of an effective carrier is an essential step in the development of a successful pesticide.

To be of optimum effectiveness, a carrier must release its active in sufficient quantities such that the environment of the targeted site maintains the minimum concentration level needed for the active's intended use. If the concentration of the active falls below this minimum, it will cease to be effective. If the carrier releases the active too quickly, several problems can occur. First, the concentration level in the surrounding environment can exceed certain minimum safety standards. When this happens, unacceptable hazards can arise. Secondly, if the carrier releases the active ingredient in amounts in excess of what is needed, the carrier will deplete itself in a shorter amount of time. In addition, some actives break down and become inactive in a relatively short period of time when subjected to hydrolysis and photolysis and therefore should not be released too quickly. As a result, there can be an overall reduction in the effective life of the pesticide, which in turn, means more frequent applications.

Some carriers currently exhibit quick release characteristics but do not supply long-term control. Conversely, other carriers which provide long-term control are not capable of producing an initial quick response. Thus, the only way to vary the control of the product is to vary the application rate. For example, to achieve a quick response with a slow release product involves increasing the initial application rate, which in turn actually wastes the active ingredient since the long-term effect will be extended beyond the initially desired period of control.

To help reduce these problems, the Applicant has invented an improved carrier which allows for controlled release of the active ingredient in a desired pattern. This is achieved by combining preselected quantities and sizes of varying corncob fractions which exhibit different release rates. By combining cob fractions in a preselected manner, a carrier can be designed which can have a slow release rate, a fast release rate or a combination of the two.

Dow Chemical previously produced a product known as Dursban 10CR which allowed the controlled release of an active by impregnating a plastic pellet with the active. One of the drawbacks to this prior art product was that the pellet was not quickly biodegradable and would therefore remain in the environment for quite some time. This product is no longer marketed.

It is an object of the present invention to provide a carrier which, when treated with a particular active ingredient, will provide an effective mechanism for releasing the active ingredient in a predetermined and desired pattern. It is also an object of the present invention to provide such a carrier which allows controlled variations in the slow and quick release concentrations of the active ingredient. It is a further object of the present invention to provide such a carrier which has an organic composition which will act as a bait when exposed to certain target organisms and which biodegrades.

Other objects and advantages of the present invention will be apparent from a review of the following specification, tables and graphs.

SUMMARY OF THE INVENTION

The present invention consists of an inert carrier for chemicals and the like which has improved and controlled release characteristics. The present invention also has proven bait like properties for certain insects, notably mosquito larvae. The carrier is comprised of selected sizes and fractions of ground corncobs which, when combined, yield a product with a planned and desirable release of the chemical and/or an attracting capability for the targeted organism.

A corncob consists of four principle parts which are arranged concentrically about one another. The center portion of a corncob is a very low density material called the pith core. Surrounding this is a very hard section called the woody ring which is in turn surrounded by the coarse chaff portion and the fine chaff portions, respectively. The coarse and fine chaff portions form the sockets for anchoring the corn kernals to the corncob. The normal methods of grinding the corncobs produces a mixture of all four of the above-mentioned portions. It is possible, however, to separate the denser woody ring material from the lighter pith and chaff portions of the cob.

The release of chemicals from a particular size and fraction of ground corncob will vary depending upon the individual characteristics of that chemical, however, it will be shown that predictable patterns exist and are utilized in the invention. In general, if a slower release is required, the use of a larger particle size of the same fraction will produce the desired result. In addition, the release rate is also dependent upon the type of cob fraction being used. The release is slower from an equivalent or larger size woody ring particle when compared to fine and coarse chaff and pith.

If a faster release is desirable, the reverse of the above should be followed that is, the substitution of a smaller particle size of the same fraction and/or the substitution of pith and fine and coarse chaff for woody ring.

The length of residual activity can be extended or the period of rapidly increasing chemical concentration can be shortened for a given amount of chemical by adjusting the relative concentration of chemical on the individual component carriers and the ratios of the various component carriers to each other.

Having the ability to control the slow and quick release characteristics of the carrier in turn allows precise adaptation of the carrier to the particular active being used. By having a carrier with controllable characteristics, it can also be adapted to the particular environment in which it will be used.

The attraction, foraging and feeding behavior of certain organisms, notably mosquito larvae, towards the invention is likewise controllable. Actual ingestion of particulate matter by larvae can be controlled by selecting the particular type and limiting the amount of the particular component within the invention which is of the size preferred by the targeted species (for mosquito larvae the size range is generally 20–500 microns) or the quantity of the component which will breakdown into this size.

To achieve the desired release pattern or attraction of the present invention, it may be necessary to combine several different cob fractions of varying sizes, densities and other dissimilar properties. The desired componets may also be of a nature making them impractical or unsafe for use in an "as is" state. For example, a desirable finely ground component may be impossible to apply without a drift hazard or, a mixture of two or more component carriers may segregate because of varying size and density. In cases such as these it is desirable to produce a more homogeneous and uniform particle. This is achieved by forming an agglomerate such as a pellet which maintains the integrity of the components upon disintegration. As used in this specification, an "agglomerate" is a mass or ball of particles. A "pellet" is an agglomerate which normally has been compressed to a desired shape.

The present invention provides a mechanism for more effectively controlling the release of certain chemicals in a desired pattern. In pesticidal applications, this increases the overall effectiveness. In addition, the bait like properties can likewise increase effectiveness by exposing the targeted organisms to a lethal concentration with more certainty.

The ability of the present invention to slow the release of chemicals into water or water systems is also a useful tool in limiting the rapid migration of excess concentrations of chemical into the soil system and the accompanying ground water. Under some conditions this unwanted excess may prohibit or restrict the application of a particular chemical at a desired location. This may be a chemical applied for the purpose of pesticidal activity or the same chemical when treated as a toxic waste.

By using the controlled release carrier in a pelleted form, several additional advantages are also achieved. When applying the pellets aerially, drift problems are greatly reduced thus reducing potential contamination of nontargeted sites and greatly improving the uniformity of application to the targeted site. Furthermore, because the pellets are heavier than many currently available carriers, more uniform application rates are possible even in areas covered by dense vegetative canopies. The pelleted formulation allows the use of individual carrier components which may possess desired release characteristics or bait like properties but are too fine in particle size or have a low density thus making them impractical for application. Finally, depending onthe quality of the pellet, the pelleted form of the carrier reduces flaking and the production of fines.

A more complete understanding of the present invention can be obtained from a reading of the following description of the preferred embodiment.

BRIEF DESCRIPTION OF THE DRAWINGS

Graph A displays the relationship between release half-lives for carrier granules made from woody ring, chaff and pith fractions of ground corn cobs and the average particle size of the carrier.

Graph B plots the percent mortality of insects against days post-treatment for each of a fast release component granule, a slow release component granule and a deploy pellet.

Graph C shows the relationship between mortality and days post-treatment for standard corncob grit and a pellet in accordance with Applicant's invention.

DESCRIPTION OF THE PREFERRED EMBODIMENT

Mosquito larvae were chosen as a model target organism because of the economic and medical importance of the pest, the universal availibility, the relatively short life cycle which allows rapid repeated determinations of efficacy and because their aquatic habitat maximizes the interplay of carrier release into water with minimal interference from other factors such as soil particulates.

Chlorpyrifos, a model compound representative of the organophosphorothioate insecticides, was studied because its effectiveness on the target organism of choice at well-defined levels and because it has displayed the ability to bind with organic matter.

To establish a baseline for the comparative differences in the release rates of various corncob carriers, granular formulations of chlorpyrifos at a 2.5% active ingredient level were prepared using various corncob fractions (woody ring fraction, fine and coarse chaff and pith fractions) in different particle sizes and a clay carrier.

One hundred fifty milligram samples of the impregnated granular carriers were placed in an enclosed system which supplied a continuous source of purified water at a rate of 8 ml per minute to the granular product. The water was coarse filtered and collected in a SEP-PAK ®. Chlorpyrifos was extracted with acetonitrile and the concentration determined by gas chromatography. Each carrier was subjected to 8 to 16 extractions over a 2–14 day exposure period. At the conclusion of each exposure period, samples were removed and the concentration of the chlorpyrifos remaining was determined as a cross check against the chlorpyrifos recovered from the water phase. The release half-life and corresponding release rate constants ($K_r$) were determined from this data and are set forth in Table 1 below.

An examination of this data indicates:

1. Up to a one hundred fold difference in release rates and release half-lives for the carriers tested.

2. That even within the broad class of the carrier defined as ground corncobs, this same 100 fold difference existed.

3. A significant difference in release rates exists between various particle size ranges of the same corncob fraction.

Release half-lives for the granule or carriers made from the woody ring, chaff and pith fractions of the ground corncobs were plotted against the average particle size of the carrier. With the exception of the largest particle size of the woody ring carrier for which a defined release half-life could not be determined accurately, a linear relationship of release rate to particle size was demonstrated, as indicated in Graph A. The plot of the woody ring fraction shows a steeper slope than that of the chaff and pith fractions thus indicating a slower release for woody ring fractions of corresponding size.

By generating these graphic representations (or their algebraic equivalents) it is possible to project a release rate constant and a half release life for similar carriers and other chemicals, as shown in Table 2.

As can be seen from Graph A, within the lower range of release rates, it is possible to substitute a woody ring component for the fine and coarse chaff components and vice versa to achieve the same half release life. For example, if a release half life for chlorpyrifos of 3 days is desired, either a fine and coarse chaff component of approximately 1.5 mm may be used or a woody ring component of approximately 0.7 mm could be substituted.

In some situations, such as temporary breeding sites containing large populations of mosquito larvae in the last stages of development prior to emergence, it may be desirable to obtain a very rapid, onetime kill to prevent the emergence of the adults without the need for extended control. In other cases, a potential breeding site may be most accessible during a period when the water is cold and eggs have not hatched. In the former case, a product with a very rapid release and no residual control could be the most desirable while in the latter, excessive amounts of active ingredient released prior to hatching of the eggs and the appearance of larvae would be wasteful. Thus, a product with a gradual release which allows the accumulation of the active to the level needed for control after egg hatch would be the more advantageous formulation.

A similar situation would exist with weed populations. Germination of seeds is triggered by a combination of factors such as, soil moisture and temperature. While a herbicide may be effective on several weed species, the active ingredient must be present at the required concentration during the proper stage of the plant's development. Climatic conditions may stimulate the germination of one susceptible weed species and then delay the time of germination of a second species past the period of effective herbicide concentration. Other factors such as, light, soil porosity, high rainfall and irrigation may also promote movement of the active ingredient through the soil and out of the effective placement zone. Control of the release of the active ingredient from the granular carrier would provide a mechanism for delaying the movement of the active ingredient through the soil column.

The method of formulating the agglomerated controlled release carrier can be relatively simple when the behavior of the active ingredient is well known, fairly consistant over the set of environmental conditions defined, and the control parameters are simple, thus generally requiring only basic mathematics. As the control parameters become more complex, the environmental restrictions greater and available data on the behavioral aspects of the chemical less well defined, more sophisticated calculations involving computer generated formulae and/or experimentally determined recombinations are required.

The general procedure involved in the determination of the level(s) of active ingredient, corn cob fraction(s) and size(s) to be used are:

1. Identify the concentration of the chemical required for control of the targeted specie(s).

2. Define as much as possible the limitations of use. For example, the maximum percent of active ingredient permissible in the finished formulation, the maximum single does of active ingredient allowed per application, etc.

3. Define the limits of the targeted environment and the impact on the removal or decomposition of the active ingredient. For example, water depth, pH, microbial population, temperature, etc.

4. Identify the overall control pattern desired and convert to active ingredient concentrations required, in the targeted environment.

5. Convert concentrations required in targeted environment to weight of active ingredient per area.

6. Apply the formula $100-(1/e\lambda t)$ (weight of active ingredient available for application) with the available carriers to determine which ones will provide the necessary concentration of active ingredient in the allowable time.

$e = 2.71828$ $\lambda = 0.693/T_{\frac{1}{2}}$ $T_{\frac{1}{2}}$ = half release life in appropriate units of time $t$ = time limitation for first control level 7. If the desired control pattern is a single knockdown, the selection process is essentially complete when the carrier which provides the required kill with the least amount of active ingredient from Step 6 above is chosen. Because the selection of carrier and quantity of active ingredient has not taken into account removal of active ingredient from the targeted environment during the release process, additional active ingredient must be included. The amount can be determined experimentally in actual trials, identified by applying, if known, the decomposition/removal constant for the active ingredient under the environmental conditions specified in an algebraic form, or can be approximated by applying the decomposition/removal constant to the total amount of active ingredient released by the carrier in the designated time period and dividing by two.

8. If extended control is required, the concentration of active ingredient for control of the targeted species should be determined. The amount of active ingredient displaced by decomposition and releated processes at that concentration should then be determined. An amount of active ingredient equal to or greater than this displaced amount must be replaced by the slower releasing component(s). Again, this decomposition/removal rate constant can be determined experimentally or, if know, the decomposition/removal constant applied mathematically. The remainder of the amount of active ingredient permissible to be applied is then formulated on a carrier or several carriers for which release rates are known, at varying percentages, such that this amount of active ingredient removed when the target environment is at the threshold concentration is replaced by an equivalent or greater amount of freshly released active ingredient. Because the additional impregnated carrier(s) will also be releasing active ingredient from first contact with the water, the amount of active so released initially should be calculated, subtracted from the quantity originally designated as fast release and added to a slow release component to extend further the residual activity.

As can be seen in Step 8, the calculations and readjustments can become complicated especially if more than two component carriers and/or percentages of active ingredient are used. In situations such as these, the mathematical calculations and selection of the optimum combination is most efficiently handled by sophisticated electronic computing devices.

Simplistic utilization of this principle is possible in a basic two component system by identifying the minimal amount of active ingredient required to meet the quick control requirement when formulated on the quick kill component, observing the length of time this provides control and then formulating the remainder of active ingredient on a slower releasing component which provides an observable but marginal level of control for an extended period when used alone.

Once the calculations for the amount of active ingredient to be impregnated on the component carriers has been completed the agglomerated carrier is formed as follows:
1. Impregnate the individual components with the desired amount of active ingredient.
2. Combine these component carriers in a mixing process.
3. Transfer the resultant mix to the agglomerating equipment, being careful to avoid conditions or equipment which would promote separation of the component carriers.
4. Agglomerate the mixture.

To produce the carrier when only bait like properties are desired, several options are available:

1. Obtain a quantity of ground corncob containing fine chaff, coarse chaff or fine and coarse chaff plus pith preferably of a size 20 mesh or finer.
2. Agglomerate the resulting product and coat with the active ingredient, or
3. Impregnate the ground corncob components with the active ingredient and then agglomerate, or
4. Blend the active ingredient with the ground corncob component(s) and then agglomerate.

In the samples produced for the applicants' testing, various California Pellet Mills were utilized ranging from 2 to 30 horsepower. However, other available equipment will also produce satisfactory agglomerates. It should be noted that one method of agglomerating may be more preferable than another in specific instances as some chemicals may not tolerate heat generated by certain processing techniques while other chemicals may be sensitive to the introduction of binding agents employed in alternative processing methods.

The size range of pellets produced varied from approximately 1/16 inch in diameter to approximately ¼ inch in diameter. The majority of the formulations were produced as ⅛ inch diameter pellets as this appeared to be the optimum size which would allow incorporation of the woody ring components desired, provided a particle capable of being utilized by the majority of the application equipment, and generate tolerable production temperatures and rates.

EXAMPLE I

A bioassay was conducted to test whether the same measured differences in the release of active ingredient into a stream of flowing water as described above would also occur in a static environment. If so, this would provide an effective mechanism for designing formulations with a specifically desired pattern of release. In addition, testing could then be done to determine the accuracy of predicting the relative speed of release using projected rather than experimentally determined release rate constants.

To test the present invention, typical mosquito larvae habitat were constructed by lining wooden, one meter square boxes with polyethylene film and sod. The boxes were then filled with 200 liters of water and allowed to stand for several days. Mosquito larvae, predominantly of the species *Culex restuans,* were field collected and introducted into each simulated breeding pool following treatment with the specified 2.5% chlorpyrifos formulations described below. This was done using larvae cages consisting of one liter plastic containers with chiffon covered cutouts on the bottom and sides for water circulation. Floatation rings were placed around each container and each of the cages was charged with 25 3rd and 4th instar larvae. Three cages were placed in each pool to provide replicated data. Mortality was defined as a lack of movement when the larva was removed from the bioassay cage using a pipette.

The key formulations evaluated all included 2.5% by weight of the mosquito larvicide chlorpyrifos. These formulations used the following carriers: a bentonite clay commercially available granular formulation as a standard; a −10 +12 mesh size woody ring corncob carrier; a −10 +12 mesh fine and coarse chaff and pith corncob carrier; a −30 mesh fine chaff corncob carrier; a −30 mesh fine and coarse chaff and pith corncob carrier; a woody ring carrier consisting of a mixture of mesh sizes identified in the trade as a nominal −8 +14 mesh; and, a pellet containing approximately 75% by weight of −30 mesh fine chaff containing 0.66% chlorpyrifos and 25% by weight of −10 +12 mesh woody ring cob at 8.0% chlorpyrifos which, when combined, yielded a carrier with an overall concentration of 2.5% chlorpyrifos. Chemical release rate constants were determined in the laboratory for the standard clay carrier, the −10 +12 mesh size woody ring and the −30 mesh fine chaff carrier. Comparative release rates were projected for the −30 mesh fine and coarse chaff and pith carrier, the −10 +12 mesh fine and coarse chaff and pith carrier, and the mixture of woody ring granules identified as 814 mesh.

The results of this testing are presented in Table 3.

As indicated by the data presented, the speed and level of control demonstrated by the various carriers, with the possible exception of the −10 +12 mesh fine and coarse chaff and pith, reflects the relative positions of the release rates of the carriers, as measured by the laboratory chemical determinations or projected from the plot generated from the laboratory data. Thus, the carrier with the highest release constant (shortest half-life) gave the quickest control.

The divergence of the −10 +12 mesh chaff carrier can be explained by the difficulty in accurately weighing out the small quantities of carrier required for the meter square pools (0.17 grams each) and to a unique property of some organic carriers including the various corncob fractions which is a prerequisite for releasing active ingredient in a desired pattern with a combination of component carriers containing differenct levels of the active ingredient.

Unlike clay and some other mineral carriers, chlorpyrifos when applied to organic carriers will not migrate from granule to granule to reach an equilibrium level following impregnation. Clay, for example, when impregnated with chlorpyrifos to a 5% level and then mixed in a one-to-one ratio with unimpregnated clay granules, will reach an equilibrium such that an individual granule will contain approximately 2.5% chlorpyrifos by weight.

This property of certain chemicals to bind to organic matter is well-known within the industry. The rates of many such materials when used as pesticides and applied as liquid formulations incorporate label directions specifying higher rates, depending upon organic matter content, to overcome this. Examples of such chemicals include; atrazine, dicamba, cyanazine, pendimethalin, propachlor and trifluralin, herbicides, chlorpyrifos, temephos insecticides.

In preparing granular formulated carriers of this type and carrier, extreme care must be taken to ensure uniform distribution when impregnating with low levels of active ingredient, as rapid evaporation of solvent may result in uneven distribution within the mix.

The pelleted formulation demonstrated the nonmigration of the active ingredient from the slower release component to the faster release component despite the fact that the concentration of chlorpyrifos was 4 times greater in the slow release fraction and the ratio of fast release component carrier was 3 to 1 by weight. This is evidenced by examining the nearly identical levels of control shown by the pelleted formulation with 80% of its active ingredient concentration on the −10 +12 woody ring carrier and the −10 +12 woody ring carrier alone.

These results further demonstrate that the nonmigration is not a temporary condition, as these tests were conducted with material which had been in storage for over 14 months. Thus, the controlled release pattern of the present invention is stable over prolonged periods of time.

EXAMPLE II

A pelletized carrier according to the present invention was tested in conjunction with a commercially available granular chlorpyrifos larvicide. The commercially available product consisted of 1% granular chlorpyrifos on a MP-77 Celatom carrier. The pelletized cob carrier, according to the invention, was comprised of −30 mesh fine and coarse chaff and pith which also contained 1% chlorpyrifos.

The pools used for testing were permanent or semipermanent water holding areas generally classified as continuous breeders, that is, the environmental conditions of these sites were such that local mosquito species, which are capable of laying eggs throughout the summer, would utilize these pools on a continuous basis until weather conditions stopped egg production. The pools varied in size with surface areas of approximately 20 to 350 square feet and average water depths from 4 inches to 24 inches.

Nine pools were verified as mosquito breeding sites with each of the pools containing mosquito lavae. Three of these pools served as untreated controls. Three were treated with the 1% chlorpyrifos on the Celatom carrier, and three were treated with the pelleted formulation which had been assayed at 0.94% chlorpyrifos. The application rate was 0.05 pounds of active ingredient per acre and was based upon the measured surface area of the pool and the assayed level of the granule. The results are presented in Table 4.

As can be seen from the data in Table 4, the pelleted corncob formulation controlled the larvae as they emerged from the eggs in all three replicates until the time when there was no detectable breeding in the untreated control. Such results were not achieved with the commercially acceptable Celatom formulation. Thus, this indicates that fine and coarse chaff and pith provide a quick release mechanism which is superior to the Celatom formulation.

EXAMPLE III

A comparison test was made between the present invention and two commercially available chlorpyrifos products. The object of the test was to determine the slow release characteristics of the present invention relative to the long-term control of mosquito lavae. The two commercial products were:

1. A granular product using a −14 +20 (U.S. Series) mesh size woody ring corncob carrier with a nominal 1% chlorpyrifos guarantee. This product was assayed and found to contain approximately 0.9% chlorpyrifos.

2. A granular product using MP-77 Celatom (a coarse diatom particle) as a carrier, also with a nominal 1% chlorpyrifos guarantee. This product was assayed at 0.97% chlorpyrifos.

The third product was a controlled release pellet according to the present invention containing approximately 95% by weight −30 mesh fine and coarse chaff and pith containing 0.70 −0.75% chlorpyrifos and 5% by weight of a commercially available −14 +20 mesh woody ring cob carrier at 2.5–2.6% chlorpyrifos. The resultant pellet was assayed at 0.81% chlorpyrifos.

Ungalvanized tanks were used to prevent enhanced decomposition of the chlorpyrifos. Each tank was filled with approximately two inches of mud and debris which was obtained from a large untreated woodland pool identified as a regular mosquito breeding site. The mud and debris was then covered with 10 inches of water and maintained at this level throughout the testing period. The actual testing took place during the summer with water supply for the tanks being obtained from a flood plain mosquito breeding site. The tanks were treated at a rate equivalent to 5 pounds of formulation per acre.

Larvae cages were prepared from four inch PVC pipe cut into 12 inch lengths which were then drilled with six, one inch diameter water circulation holes and screened with a fine mesh stainless steel cloth. The cages were then suspended in the drums with heavy gauge wire. Three larvae cages containing 20 field collected larvae each were placed in the tanks. Mortality figures were recorded for 24-hour exposure intervals during this test.

Larvae used in this testing were *Culex restuans* for days 1 to 3, *Aedes vexans* for days 4 to 15, and *Culex pipiens* thereafter. An attempt was made to use primarily late 2nd and early 3rd instar larvae, however, during the first 15 days of this testing, large numbers of 3rd and 4th instar were used because of larvae scarcity. Approximately 10–15% of these matured to the pupae stage during the 24-hour observation periods. Because these larvae would be relatively inactive and not feeding, pupated larvae were deleted from the initial replicate population in which they appeared.

The results of this testing are indicated in Table 5. During the course of this testing, both rooted aquatic vegetation and algae became established, thus indicating that the artificial environment created for these tests was very representative of typical woodland pool conditions. The tanks were intentionally left uncovered to simulate as much as possible a "natural" situation, and eventually they became sites for the deposit of egg rafts by adult mosquitos. Although untreated tanks were initially used as controls, it soon became apparent that this was impractical as 1st instar larvae would appear in the control test cages thus giving a net gain in population. Despite this increase, natural mortality in the untreated control tanks was recorded for the first 7 days and typically showed 0–5% mortality.

All products tested during this period demonstrated an efficacy greater than 90% within 24 hours of application, as shown in Table 5, when applied at the higher rate of 5 pounds per acre. The commercial Celatom formulation showed a loss of effective control 12 days after treatment.

The pelleted formulation provided 90% plus control for 18 days and was therefore superior to the commercially acceptable Celatom formulation in length of residual control and approximately equal to the Celatom in meeting the commercial requirement of 90% plus control within the first 24 hours following application.

The −14+20 mesh woody ring carrier provided the 90% plus level of control for approximately 33 days at this high label rate.

This test series demonstrated:

1. The ability of the invention to provide a mechanism of releasing the active ingredient such that both a quick kill and residual control could be provided.

2. That less active ingredient was required with the present invention (0.81% chlorpyrifos×5 lbs. product/acre=0.0405 lbs. chlorpyrifos/acre) to provide overall control superior to the Celatom standard (0.97% chlorpyrifos×5 lbs product/acre=0.0485 lbs chlorpyrifos/acre).

3. That while this combination of carriers and the levels of chlorpyrifos impregnated on them was superior to the Celatom standard, the tested pelleted formulation did not provide the length of residual control demonstrated by the −14+20 mesh woody ring carrier. This is to be expected as both the latter products utilize the same slower release carrier with the pelleted formulation delivering less than 15% of the amount of chlorpyrifos of the straight −14 +20 mesh woody ring carrier through this slower releasing carrier.

EXAMPLE IV

Testing was conducted in August 1982 in a manner similar to that cited in Example III with these changes;

1. The water used for testing was of a higher pH (9±0.1) which encouraged more rapid decomposition of chlorpyrifos when in the dissolved state.

2. The larva used were a uniform population of 2nd and 3rd instar *Culex pipiens.*

3. The previously tested standard −14 +20 mesh woody ring corncob carrier, which was assayed at 0.91% chlorpyrifos, was applied at 0.025 pounds of active ingredient per acre based on the assay. This is the minimum application rate usually indicated on commercial granular product labels.

4. A pelleted carrier was tested containing approximately 15% by weight −14 +20 mesh wood ring at 2.57% chlorpyrifos and approximately 85% by weight −30 mesh fine and coarse chaff and pith fractions at 0.73% chlorpyrifos. This product was assayed at 1.0% chlorpyrifos and applied at 0.025 pounds of active ingredient per acre.

5. An amount of the slower releasing component (−14 +20 mesh woody ring assayed at 2.57% chlorpyrifos) was tested which was equal to the amount delivered by the pelleted formulation when applied at 0.025 pounds of chlorpyrifos per acre, that is, 15% by weight of the total amount.

6. An amount of the quicker releasing component (−30 mesh fine and coarse chaff and pith assayed at 0.73% chlorpyrifos) was tested which was equal to the amount delivered by the pelleted formulation when applied at 0.025 pounds of chlorpyrifos per acre, that is, 85% by weight of the total amount.

The results of the August testing are presented in Graphs B and C.

The August testing indicated that the amount of active ingredient by either of the individual slow or quick release components was inadequate by itself to provide a required 90% kill rate within 24 hours. As shown in Graph B, however, the chlorpyrifos release and accumulation from the quick release component (the coarse and light chaff and pith) was sufficient to provide the required level of efficacy on days 2 and 3. Thus, while neither component individually was able to maintain a sufficiently prolonged 90% plus kill rate, their combined effect did result in the desired kill rate.

In Graph C, a comparison of the pelletized product with the 1420 woody ring formulation indicates that the Applicant's pellet had an initial kill rate almost four times that of the standard 1420 woody ring carrier. At the lower application rate of 0.025 pounds of active ingredient per surface acre and with the high pH levels, the 1420 woody ring formulation failed to provide the minimum level of 90% control. The pelleted carrier, on the other hand, demonstrated 96.7% control at 24 hours and maintained a 90% plus control level for 8 days.

As indicated in Graph B and C, between days 11 and 13 of the testing, all four treatments showed noticeable increase in efficacy with the pellet formulation going from approximately a 22% kill rate on day 10 to a 95% kill rate on day 16. An examination of weather records indicated that an acid rain (pH 4.0) fell beginning the evening of the 11th day of the trials and continued through the 12th day. This was the only appreciable rainfall during the course of the experiment and resulted in a significant pH reduction in the test tank water to an average value of 7.80. As is shown in Table 6, the decomposition rate of chlorpyrifos is considerably greater at an elevated pH. The theory proposed to explain the resurgence of control is that the lowered pH slowed the decomposition rate of chlorpyrifos to below the rate of the chlorpyrifos being released from the two products, thus allowing an accumulation of the chlorpyrifos which resulted in higher concentration levels and increased efficacy.

In this test, the commercially acceptable corncob woody ring product failed to provide either the required 24 hour level of control or the residual activity desired.

As demonstrated here, one advantage of the present invention is the ability to control the amount of active ingredient released such that variations in environmental conditions affecting performance can be more adequately compensated for without increasing the total amount of active ingredient. In addition, this demonstrates the present invention's ability to provide acceptable control at lower application rates by optimizing the quicker releasing fractions of the carrier.

EXAMPLE V

Field testing was also conducted upon the present invention, During June 1982, approximately 1,300 acres were treated with a pelletized formulation meeting the same general specifications of slow and fast release components as outlined in Example IV.

The test site was a flood plain area containing a number of pools created by heavy spring rains and river flood water impounded by a series of dikes and natural obstructions. Three pools with an average depth of 12 inches and a surface area of approximately 200 square foot each were chosen for the testing.

The density of the larva population was determined using the general survey technique of randomly dipping a standardized aquatic dipper into each pool and counting the number of larvae present per dip.

The population was found to be non-uniform in development with pupae as well as 2nd through 4th instar larvae being present. This type of a mixed population is not atypical. The presence of pupae and the more mature larvae states are indicative of the need for a quick acting formulation to prevent the emergence of adults.

The area was treated aerially using a Bell G-47 helicopter equipped with Simplex Seeder application gear at a rate of 5 pounds of formulation per acre. Control was measured as the percent reduction in mosquito larvae relative to pretreatment population counts.

Tests results are presented in Table 7. The field test data of Table 7 confirmed the other results in that it demonstrated that under actual field conditions the present invention does provide the high level of quick control which is required to prevent the emergence of an adult brood when larvae are approaching this state of development.

EXAMPLE VI

Another factor in achieving a high kill rate with mosquito larvae or any insect involves getting the active ingredient as close as possible to the targeted species. Once the pellet carriers are placed in the water, they each act as an individual source of the active ingredient. Due to the release of the active from the carrier into the water, a concentration gradient is set up around the carrier. The concentration of active is highest in the area immediately surrounding the carrier and decreases as the distance from the carrier increases until an equilibrium level is reached in the water. Thus, the closer the mosquito larvae can be drawn to the carrier, the higher the concentration of the active ingredient and consequently the higher the chance of achieveing a quick kill of the lavae.

Early in the course of field testing, an unexpected behavior was observed in mosquito larvae which were exposed to corncob carriers containing specific types and sizes of cob fractions. If the larvae had access to formulations containing finely ground fine chaff or fine and coarse chaff and pith, such as the −30 mesh size carriers, the larvae would deviate from the normal pattern of remaining near the water surface where they remain in a resting/feeding position the majority of the time. Instead, the larvae would orient themselves around the pelleted carrier located on the bottom of the pool. On several occasions, field collected larvae were transferred into glass containers containing pelleted formulations of −30 mesh material for more detailed observations. The larvae duplicated the behavior observed in the field and appeared to be ingesting or foraging on the disintegrated pellet. By ingesting the pellet particles the highest contact with the active became possible.

Upon further testing it was found that this ingesting and foraging behavior was greatest when the pith and fine and coarse chaff fractions were present in sizes of −20 mesh. If the particles were slightly larger than this there was still attraction to the carrier but the particles were too large for the developing larvae to ingest. Beyond this range there was less attraction to the carrier. In addition, this ingesting and foraging behavior was markedly reduced when the larvae were exposed to woody ring fractions in the same range of particle sizes. Thus, it became apparent that the ingesting and foraging behavior was a direct result of the selection, processing and grinding of the cob fractions prior to their introduction into the water system.

To further substantiate the above, further field testing was done. A woodland pool was located which contained a large amount of green algae, a natural food source. Because the midgut of the mosquito larva is transparent, visual observation indicated that the larvae were feeding heavily on the algae with approximately 80 to 90% of them displaying a green midgut. The pool was approximately 864 feet in surface area with a mid-pool depth of approximately 12 inches and an average depth of 8 inches. Larvae from the pool were later collected and identified from a 58-specimen sampling to be the specie *Aedes canadensis*. The pool was treated at a rate of between 5 and 10 pounds per acre with a pelleted formulation containing −30 mesh light and coarse chaff with no active ingredient. A re-examination of the pool 24 hours after treatment revealed that a majority (approximately 75 to 90%) of the larvae collected now displayed a brown to light tan midgut. This was the same color as the pelleted cob carrier.

A 20-dip sampling of the pool was taken to determine the mosquito population dynamics. The pretreatment survey showed that a large share of the population was nearing the low or non-feeding stages of development, that is 4th instar and pupae. The pool was then treated with a pelleted product containing −30 fine and coarse chaff formulated with the biological control agent *Bacillus thuringiensis* var. *israelensis* (*B.t.i.*) incorporating into the pellet at an original concentration equivalent to 350 AA u nits per milligram of product. The rate of finished formulation applied was approximately 1.25 pounds per acre which is the lowest equivalent labeled rate of the wettable powder formulation on an active ingredient basis. The pool was sampled 24 hours after treatment using the same technique specified previously. The results are presented in Table 8.

The toxicant *Bti* is a protein endotoxin produced by certain bacteria and must be ingested by the moisquito larvae to be effective. Mosquito pupae do not feed and 4th instar larvae feed little which limits the effectiveness of *Bti* in controlling larvae broods nearing adolescent maturity. Examination of the data presented in Table 8 indicates that the pelleted −30 mesh corncob carrier with *Bti* did provide a reduction in larval population. The increase in pupal count indicates that a large share of the original population was in the low feeding 4th instar stage. Despite this, even if all post treatment pupae are counted as survivors of an exposed larval population, the minimum level of control demonstrated is 75.2%. In addition, of the surviving larvae found in the post treatment sampling, 6.5% displayed green midguts indicating algae as a food source, and approximately 26% displayed a transparent midgut indicating little if any feeding.

The significance of these test results is even greater when it is noted that past efforts to produce a heavyweight granular *Bti* formulation have been unsuccessful when applied to water deeper than approximately 6 inches. Most mosquito larvae feed near the water surface on floating or suspended particulate organic matter. In general, formulations of *Bti* applied as liquids have employed additives to aid in the suspension of the endotoxin and/or decrease the rate of settling. Solid formulations have included doughtnut shaped floating rings and floating wax prills coated with *Bti* and the like as methods of keeping the ingested toxicant in the normal feeding zone. Because of the bait like properties of the finely ground organic materials in the pellet, efficacy with the *Bti* was possible with the heavyweight carrier in water deeper than 6 inches.

This bait like property will also increase efficacy of traditional chemical larvicides as a result of the actual ingestion of the impregnated components of the pellet and/or by attracting the larvae into the gradient of higher chemical concentration surrounding the disintegrating pellet. As used in this application, "bait" means a carrier that is capable of attracting or being ingested by the targeted species.

EXAMPLE VII

Pellets containing −30 mesh fine and coarse chaff and pith were prepared. *Bti* formulations were then produced by coating the exterior of the pellets with food grade vegetable oil and then introducing the finely divided basic fermentation product containing the *Bti* endotoxin, known in the trade as *Bti* primary powder. The resulting product thus included the *Bti* primary powder which was coated on the pellets exterior at a level of approximately 5% or 350 AA units per milligram of product.

In each of three simultaneous replicates, sterile, one foot square larval-rearing pans were filled to a depth of 1½ inches with room temperature well water (3.5 liters). One hundred early phase, 3rd instar *Aedes aegypti* larvae were then added without food. A pre-weighed quantity of pellets were finally added, representing the application rate of choice. Dead larva were removed at 2, 4 and 24 hour intervals and mortality recorded. One hundred new larvae were introduced at each 24 hour interval and the removal and recording process was repeated. The results are presented in Table 9.

In this testing, the attraction to and foraging activity of the larvae around the pellets was again observed. As shown in the data presented, coating the active ingredient on the exterior of the pellet does not diminish the effectiveness of the *Bti* and does not reduce the bait like properties.

Because *Bti* must be ingested to be lethal, this is an extreme test of the attractiveness of the ground corncob and the stimulation of foraging behavior in the larvae. Coating the exterior of the pellet with other toxicants which kill by contact, as well as ingestion, would also be improved as the larvae are concentrated in the zone of greater pesticide concentration surrounding the pellet.

EXAMPLE VIII

*Bti* primary powder was mixed with a −20 +30 mesh fine and coarse chaff corncob fractions to a concentration of 2.5% and then pelleted. Eight plastic containers were charged with water to a depth of 5 inches and treated with the 2030 cob pellets containing the *Bti* at a rate equivalent to 2.5 pounds of finished formulation per acre. Fifty larvae were then introduced. Mortality was recorded at 24 hours, the live larvae removed and 50 additional larvae added. Mortality was then recorded at 48 hours after treatment. The results are presented in Table 10 and indicate that the 2030 light and coarse chaff pelletized carrier was attractive to the larvae and provided acceptable control.

CONCLUSION

The controlled release agglomerated or pelletized carrier using selected combinations of individual slow and quick release carrier which do not allow migration of the active ingredient within the pellet and which possess different release rates demonstrates an effective mechanism for providing extended control with no loss of the desired high initial kill rate. This improved carrier also allows for a more efficient and environmentally judicious use of the active ingredient. As shown in the test results presented, the rate per acre of active ingredient need not be increased to compensate for a low initial release. Rather than increasing the rate, a fixed quantity of active ingredient formulated on a rapidly releasing carrier component and known to provide acceptable initial control in the desired time frame can be incorporated into a finished product with the remainder of the active ingredient being impregnated into the slower release component. This resultant carrier thus provides acceptable initial and long-term control through the controlled release mechanism of the carrier.

In addition, the test results indicate that a more uniform application rate is achievable with the present carrier while reducing off site drift and handling problems.

While the above testing was done in conjunction with the control of mosquitos with the use of chlorpyrifos as the active ingredient, it should be understood that the present invention is capable of being used with any type of active ingredient which can be applied to an inert carrier. For examples, the active ingredients may be other insecticides, herbicides, or the like.

In addition, while it is preferable to mix the active or actives with the individual slow release and quick components prior to agglomerating or pelletizing, the active may be applied to the pelletized carrier, according to the present invention. In this latter embodiment the bait characteristics of the present carrier are still present during use of such carrier.

The invention having been described in considerable detail, it should be understood that the above examples are for illustration purposes only and are not intended to limit the scope of the invention in any way. Furthermore, it should be understood that minor modifications of the invention can be made without departing from the scope and sphere of the following claims.

TABLE 1

Experimentally determined release rate constants and release half lives for chlorpyrifos granules. (measured amounts of chemical released into water)

| CARRIER | $k_r$ (min. $^{-1}$) | T ½ (days) |
|---|---|---|
| 2448 Bentonite Clay Corncobs | $1.046 \times 10^{-4}$ | 4.6 |
| Fraction 25/30 LRC | $4.01 \times 10^{-4}$ | 1.2 |
| Fraction 12/14 LRC | $1.504 \times 10^{-4}$ | 3.2 |
| Fraction 6/8 LRC | $6.78 \times 10^{-5}$ | 7.1 |
| Fraction 25/30 GOC | $3.438 \times 10^{-4}$ | 1.4 |
| Fraction 12/14 GOC | $2.86 \times 10^{-5}$ | 16.8 |
| Fraction 10/12 GOC | $2.43 \times 10^{-5}$ | 19.8 |
| Fraction 6/8 GOC | $< 4 \times 10^{-6}$ | 119+ |
| Fraction - 30 Fine Chaff | $2.674 \times 10^{-4}$ | 1.8 |

GOC = Woody Ring
LRC = Fine and coarse chaff and pith

TABLE 2

Predicted* and experimentally determined release rate constants and release half lives for chlorpyrifos formulations tested in bioassays.

| CARRIER | $k_r$ (min. $^{-1}$) | T ½ (days) |
|---|---|---|
| 2448 Bentonite Clay Corncobs - Size Type | $1.046 \times 10^{-4}$ | 4.6 |
| Fraction - 30 LRC | $4.81 \times 10^{-4}$ | 1.0 |
| Fraction 10/12 LRC | $1.266 \times 10^{-4}$ | 3.8 |
| Fraction - 30 Fine Chaff | $2.674 \times 10^{-4}$ | 1.8 |
| Fraction 10/12 GOC | $2.43 \times 10^{-5}$ | 19.8 |
| Fraction 8/14 GOC | $3.22 \times 10^{-5}$ | 14.9 |
| Fraction 14/20 GOC | $6.59 \times 10^{-5}$ | 7.3 |

GOC = Woody Ring
LRC = Fine and coarse chaff and pith

TABLE 3

Comparison of the larvicidal activity of 6 corncob formulations and bentonite Dursban 2.5 G tested at the same application rate of 1.5 lbs product/A (Bioassay I).

ACCUMULATED MEAN PERCENT MORTALITY (0.17 g/200 l pool)

| EXPOSURE TIME (h) | BENTONITE | −30 LRC | 10/12 LRC | 8/14 LRC | 10/12 GOC | PELLET −30 Fine Chaff +1012 GOC | −30 Fine Chaff | CONTROL |
|---|---|---|---|---|---|---|---|---|
| 1 | 1.3 | 1.4 | 0 | 0 | 0 | 0 | 0 | 0 |
| 2 | 1.3 | 2.7 | 0 | 0 | 0 | 0 | 0 | 0 |
| 3 | 1.3 | 8.1 | 0 | 0 | 0 | 0 | 0 | 0 |
| 4 | 1.3 | 50.0 | 0 | 0 | 0 | 0 | 0 | 0 |
| 5 | 2.7 | 87.5 | 0 | 2.7 | 1.4 | 0 | 0 | 0 |
| 6 | 2.7 | 95.9 | 0 | 2.7 | 1.4 | 0 | 0 | 0 |
| 7 | 2.7 | 97.3 | 1.4 | 4.2 | 1.4 | 0 | 13.5 | 0 |
| 8 | 2.7 | 97.3 | 1.4 | 12.5 | 1.4 | 0 | 59.5 | 0 |
| 24 | 100.0 | 98.6 | 1.4 | 30.6 | 4.2 | 0 | 100.0 | 0 |
| 30 | 100.0 | 100.0 | 12.7 | 36.1 | 4.2 | 0 | 100.0 | 0 |
| 48 | 100.0 | 100.0 | 49.3 | 47.2 | 8.6 | 16.4 | 100.0 | 0 |

GOC = Woody Ring
LRC = Fine and coarse chaff and pitch

TABLE 4

LARVAL BREEDING DATA (rate tested 0.05 lbs AI/A)

Number of Replicates Breeding

| | −30 Mesh 0.94% Chlorpyrifos Pellet | MP77 1% Celatom | Untreated Controls |
|---|---|---|---|
| Pre-Application | 3 | 3 | 3 |
| 15–17 hours | 0 | 1 | 3 |
| 24–26 hours | 0 | 1 | 3 |
| 4 days | 0 | 1 | 3 |
| 11 days | 0 | 1 | 3 |
| 18 days | 0 | 1 | 3 |
| 24 days | 0 | 1 | 3 |
| 35 days | 0 | 0 | None |

TABLE 7

| | Pre-Treatment | 6.5 Hours Post-Treatment |
|---|---|---|
| Average Number of Larvae Per Dip | 18.2 | 2.7 |
| Population Range Per Dip | 6–34 | 0–9 |
| Overall Reduction in Population (control) | 0 | 85.2% |

TABLE 5

Larvicidal activity of chlorpyrifos formulations applied at 5 lbs. finished product/A to simulated woodland pools Bioassay III.
PERCENT MORTALITY-24 HOUR EXPOSURE PERIODS

| TREATMENT | DAYS POST TREATMENT | | | | | | | | | | | | | |
|---|---|---|---|---|---|---|---|---|---|---|---|---|---|---|
| | 1 | 2 | 3 | 4 | 5 | 11 | 12 | 13 | 14 | 15 | 16 | 17 | 18 | 19 |
| Standard: Corncob Grit Carrier, Assay 0.91% | 100.0 | 100.0 | 98.3 | 100.0 | 98.3 | 100.0 | 80.0 | 93.2 | 94.9 | 100.0 | 100.0 | 100.0 | 100.0 | 93.3 |
| Standard: MP77 Celatom Carrier, Assay 0.97% | 98.3 | 100.0 | 100.0 | 100.0 | 100.0 | 100.0 | 56.7 | 57.9 | 57.6 | 37.3 | 30.5 | 33.3 | 40.0 | 38.3 |
| Multi Component Pellet[2] Assay 0.81% | 100.0 | 100.0 | 100.0 | 100.0 | N/D | 100.0 | 73.3 | 96.6 | 90.7 | 93.2 | 98.3 | 94.7 | 96.7 | 88.3 |

| TREATMENT | DAYS POST TREATMENT | | | | | | | | |
|---|---|---|---|---|---|---|---|---|---|
| | 25 | 26 | 31 | 32 | 33 | 36 | 37 | 38 | 44 |
| Standard: Corncob Grit Carrier, Assay 0.91% | 75.0 | 83.3 | 95.0 | 95.0 | 95.0 | 88.3 | 80.0 | 46.7 | 31.7 |
| Standard: MP77 Celatom Carrier, Assay 0.97% | 5.0 | 6.7 | N/D | N/D | N/D | N/D | N/D | N/D | 8.3 |
| Multi Component Pellet[2] Assay 0.81% | 10.0 | 10.0 | N/D | N/D | N/D | N/D | N/D | N/D | 6.7 |

[1]Breaks in data at 6/12, 6/26, 7/3 and 7/10 are a result of insufficient field collected larvae.
[2]Approximately 85% chlorpyrifos formulated on carrier at $k_r = 4.8 \times 10^{-4}$ min.$^{-1}$.

TABLE 6

STABILITY OF CHLORPYRIFOS DISSOLVED IN WATER

| pH EFFECT | TEMPERATURE (°C.) | pH | HALF-LIFE DAYS |
|---|---|---|---|
| TAP WATER (UNBUFFERED) | 25 | 8 | 1.5 |
| NATURAL WATER (UNBUFFERED) | 25 | 8 | 1.5 |
| PHOSPHATE BUFFER | 25 | 8 | 23 |
| PHOSPHATE BUFFER | 25 | 7 | 35 |
| PHOSPHATE BUFFER | 25 | 5 | 63 |

TABLE 8

EFFICACY TESTS OF −30 MESH CORNCOB PELLET WITH INCORPORATED BTI

|  | Pre-Treatment | Post-Treatment |
|---|---|---|
| Larva Count (average per dip) | 12.3% | .775% |
| Pupae Count (average per dip) | 1.0 | 2.275 |
| Larval Reduction | — | 93.4 |
| Minimum Control Demonstrated (all post treatment larvae counted as exposed to toxicant) |  | 75.2% |

TABLE 9

EFFICACY OF −30 MESH CORNCOB PELLETS COATED WITH 5% BTI PRIMARY POWDER

| DAY | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| @ 5 lbs/Acre | 99 | 99 | 100 | 99 | 99 | 92 | 96 | 68 | 52 | 47 | 39 | 32 | 33 | 19 |
| @ 10 lbs/Acre | 100 | 100 | 100 | 100 | 100 | 100 | 100 | 100 | 100 | 100 | 97 | 97 | 99 | 100 |

| DAY | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| @ 5 lbs/Acre | 31 | 22 | 19 | 14 | 6 | 1 | 0 |  |  |  |  |  |  |  |  |  |
| @ 10 lbs/Acre | 100 | 100 | 100 | 100 | 100 | 97 | 97 | 95 | 68 | 94 | 99 | 84 | 97 | 96 | 99 | 55 |

TABLE 10

EFFICACY TESTING OF BTI PRIMARY POWDER INCORPORATED INTO A 2030 MESH FINE AND COARSE CHAFF CORNCOB PELLET

|  | 24 Hours Post Treatment | 48 Hours Post Treatment |
|---|---|---|
| Average % Mortality | 87.8 | 98.8 |
| Range % Mortality | 74–94 | 90–100 |

What we claim is:

1. A controlled release agglomerated carrier including a quicker releasing component and a slower releasing component, said quicker releasing component comprising separated ground pith and fine and coarse chaff portions of a corncob, said slower releasing component comprising separated ground woody ring portions of a corncob, said components being combined in said carrier such that said carrier contains not more than 95% by weight of said quicker releasing component and not less than 5% by weight of said slower releasing component, said quicker and slower releasing components being a particle size that will pass through a 10 mesh (U.S. standard series) screen before being agglomerated, said quicker releasing component being impregnated with a pesticide capable of binding with organic matter at one concentration level and said slower releasing component being impregnated with a pesticide capable of binding with organic matter at a second concentration level.

2. A controlled release agglomerated carrier according to claim 1 wherein said pesticide is chlorpyrifos.

3. A controlled release agglomerated carrier according to claim 1 wherein said pesticide is an insecticide.

4. A controlled release agglomerated carrier according to claim 1 wherein said pesticide is a herbicide.

5. A controlled release agglomerated carrier according to claim 1 wherein said pesticide is *Bacillus thuringiensis* var. *israelensis*.

6. A controlled release agglomerated carrier according to claim 1 wherein said carrier acts as a bait for insect larvae.

7. A method of making a controlled release agglomerated carrier comprising the steps of combining not more than 95% by weight of a quicker releasing component comprising the separated ground pith and fine and coarse chaff portions of a corncob with not less than 5% by weight of a slower releasing component comprising the separated ground woody ring portion of a corncob, including impregnating said slower and quicker releasing components with a pesticide, mixing said slower and quicker releasing components and agglomerating the mixture of said slower and quicker releasing components.

8. A method of making a controlled release agglomerated carrier according to claim 7 wherein said pesticide is an insecticide.

9. A method of making a controlled release agglomerated carrier according to claim 7 wherein said pesticide is a herbicide.

10. A method of making a controlled release agglomerated carrier according to claim 7 wherein said pesticide is *Bacillus thuringiensis* var. *israelensis*.

11. A method of making a controlled release agglomerated carrier according to claim 7 wherein said carrier is surface coated with a pesticide capable of binding with organic matter.

12. A method of making a controlled release agglomerated carrier according to claim 7 wherein said pesticide is chlorpyrifos.

13. A controlled release agglomerated carrier which acts as a bait for insect larvae including a quicker releasing component and a slower releasing component, said quicker releasing component comprising separated ground pith and fine and coarse chaff portions of a corncob, said slower releasing component comprising separated ground woody ring portions of a corncob, said quicker releasing component being impregnated with a pesticide capable of binding with organic matter at one concentration level, said slower releasing component being impregnated with a pesticide capable of binding with organic matter at a second concentration level, said components being combined in said carrier such that said carrier contains not more than 95% by weight of said quicker releasing component and not less than 5% by weight of said slower releasing component, said quicker and slower releasing components being of a particle size that will pass through a 20 mesh (U.S. standard series) screen before being agglomerated.

14. A controlled release agglomerated carrier which acts as a bait for insect larvae according to claim 13 wherein said pesticide is *Bacillus thuringiensis* var. *israelensis*.

15. A controlled release agglomerated carrier which acts as a bait for insect larvae according to claim 13 wherein said insect larvae are mosquito larvae.

16. A controlled release agglomerated carrier which acts as a bait for insect larvae according to claim 13, wherein said carrier contains no slower releasing component.

17. A controlled release agglomerated carrier which acts as a bait for insect larvae according to claim 16, wherein said carrier is surface coated with a pesticide capable of binding with organic matter.

18. A controlled release agglomerated carrier which acts as a bait for insect larvae according to claim 17, wherein said pesticide is *Bacillus thuringiensis* var. *israelensis*.

19. A method of baiting insect larvae in a breeding area comprising applying to said breeding area a controlled release agglomerated carrier which acts as a bait including a quicker releasing component and a slower releasing component, said quicker releasing component comprising separated ground pith and fine and coarse chaff portions of a corncob, said slower releasing component comprising separated ground woody ring portions of a corncob, said components being combined in said carrier such that said carrier contains not more than 95% by weight of said quicker releasing component and not less than 5% by weight of said slower releasing component, said quicker and slower releasing components being of a particle size that will pass through a 20 mesh (U.S. standard series) screen before being agglomerated, said quicker and slower releasing components being impregnated with a pesticide capable of binding with organic matter before being agglomerated.

20. A method of baiting insect larvae in a breeding area according to claim 19 wherein said pesticide is *Bacillus thuringiensis* var. *israelensis*.

21. A method of baiting insect larvae in a breeding area according to claim 19 wherein said insect larvae are mosquito larvae.

22. A method of baiting insect larvae in a breeding area according to claim 19 wherein said carrier is surface coated with a pesticide capable of binding with organic matter.

23. A method of baiting insect larvae in a breeding area according to claim 19, wherein said carrier contains no slower releasing component.

24. A method of baiting insect larvae in a breeding area according to claim 19, wherein said carrier is surface coated with said pesticide.

25. A method of making a controlled release agglomerated carrier comprising the steps of mixing not more than 95% by weight of a quicker releasing component consisting essentially of the separated ground pith and fine and coarse chaff portions of a corncob, with not less than 5% by weight of a slower releasing component consisting essentially of the separated ground woody ring portion of a corncob, impregnating said slower and quicker releasing componets with a pesticide and agglomerating the mixture of slower and quicker releasing components.

* * * * *